(12) United States Patent
Aghassian

(10) Patent No.: US 9,211,418 B2
(45) Date of Patent: Dec. 15, 2015

(54) POSITION-DETERMINING EXTERNAL CHARGER FOR AN IMPLANTABLE MEDICAL DEVICE

(75) Inventor: Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 211 days.

(21) Appl. No.: 13/605,664

(22) Filed: Sep. 6, 2012

(65) Prior Publication Data

US 2013/0096650 A1    Apr. 18, 2013

Related U.S. Application Data

(60) Provisional application No. 61/548,446, filed on Oct. 18, 2011.

(51) Int. Cl.
  *A61N 1/37* (2006.01)
  *A61N 1/378* (2006.01)
  *A61N 1/372* (2006.01)

(52) U.S. Cl.
  CPC ............ *A61N 1/3787* (2013.01); *A61N 1/37252* (2013.01)

(58) Field of Classification Search
  CPC ............................ A61N 1/3981; A61B 1/00034
  USPC ....................................... 607/33, 61
  See application file for complete search history.

(56) References Cited

U.S. PATENT DOCUMENTS

| | | | |
|---|---|---|---|
| 7,970,477 B2 * | 6/2011 | Loeb et al. ............... | A61B 5/06 607/48 |
| 7,974,689 B2 | 7/2011 | Volpe et al. | |
| 8,010,205 B2 * | 8/2011 | Rahman et al. ..... | A61N 1/37229 607/60 |
| 8,192,398 B2 * | 6/2012 | Hoendervoogt et al. ................. | A61M 5/14276 600/424 |
| 2006/0161211 A1 * | 7/2006 | Thompson et al. ............. | 607/19 |
| 2008/0300654 A1 * | 12/2008 | Lambert et al. ................. | 607/59 |
| 2009/0112291 A1 * | 4/2009 | Wahlstrand et al. ............ | 607/61 |
| 2010/0219796 A1 * | 9/2010 | Kallmyer ...................... | 320/153 |
| 2010/0298910 A1 * | 11/2010 | Carbunaru et al. ............. | 607/60 |
| 2011/0071597 A1 | 3/2011 | Aghassian | |

(Continued)

OTHER PUBLICATIONS

Medtronic, Inc.; "RestoreSensor Neurostimulator—the Choice of Continuous Motion"; May 2011; p. 1-3; Medtronic International Trading Sárl; Tolochenaz.

(Continued)

*Primary Examiner* — Christopher D Koharski
*Assistant Examiner* — Natasha Patel
(74) *Attorney, Agent, or Firm* — Lewis & Reese, PLLC

(57) ABSTRACT

An improved external charger for an implantable medical device is disclosed in which charging is at least partially controlled based on a determined position of the external charger, which position may be indicative of the pressure between the external charger and a patient's tissue. The improved external charger includes one or more position determination elements, e.g., an accelerometer or gyrometer, and control circuitry for controlling the external device in accordance with the determined position. The determined position of the external charger can be used to control charging, for example, by suspending charging, by adjusting the intensity of charging, by adjusting a maximum set point temperature for the external charger, or issuing an alert via a suitable user interface. By so controlling the external charger on the basis of the determined position, the external charger is less likely to create potentially problematic or uncomfortable conditions for the user.

34 Claims, 9 Drawing Sheets

"Charger Face Down"    "Normal"    "Charger Face Up"

(56) References Cited

U.S. PATENT DOCUMENTS

| | | |
|---|---|---|
| 2011/0093048 A1 | 4/2011 | Aghassian |
| 2011/0105955 A1 | 5/2011 | Yudovsky et al. |
| 2011/0178576 A1 | 7/2011 | Aghassian |
| 2011/0190849 A1 | 8/2011 | Faltys et al. |
| 2012/0197322 A1 | 8/2012 | Skelton et al. |

OTHER PUBLICATIONS

Analog Devices, Inc.; "ADXL346: 3-Axis, ±2 g/±4 g/±8 g/±16 g Ultra Power Digital Accelerometer"; May 2011; p. 1-40; Analog Devices, Inc.; Norwood, MA U.S.A.

International Search Report regarding application No. PCT/US2012/057573 dated Dec. 13, 2012.

* cited by examiner

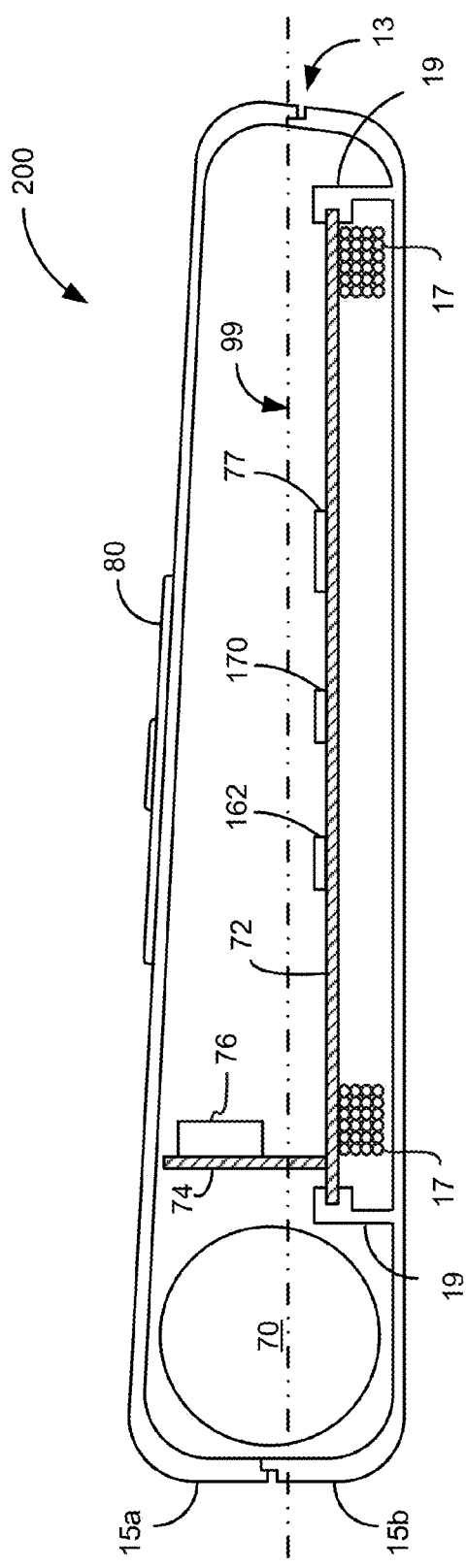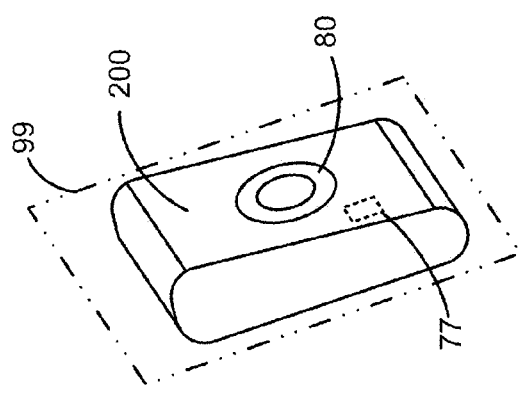
Figure 4

POSITION-DETERMINING EXTERNAL CHARGER FOR AN IMPLANTABLE MEDICAL DEVICE

CROSS-REFERENCE TO RELATED APPLICATIONS

This is a non-provisional application based on U.S. Provisional Patent Application Ser. No. 61/548,446, filed Oct. 18, 2011, which is incorporated by reference, and to which priority is claims.

FIELD OF THE INVENTION

The present invention relates generally to implantable medical device systems, and, more particularly, to an external device such as an external charger for an implantable medical device controllable on the basis of the determined position of the external charger, e.g., in three-dimensional space.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. Pat. No. 6,516,227, which is incorporated herein by reference in its entirety.

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30 formed of titanium, for example. The case 30 usually holds the circuitry and power source or battery necessary for the IPG to function. The IPG 100 is coupled to electrodes 106 via one or more electrode leads (two such leads 102a and 102b are shown), such that the electrodes 106 form an electrode array 110. The electrodes 106 are carried on a flexible body 108, which also houses the individual signal wires 112a-112p, coupled to each electrode. The signal wires 112a-112p are connected to the IPG 100 by way of an interface 115, which may be any suitable device that allows the leads 102 (or a lead extension, not shown) to be removably connected to the IPG 100. Interface 115 may comprise, for example, an electro-mechanical connector arrangement including lead connectors 38a and 38b configured to mate with corresponding connectors on the leads. In the illustrated embodiment, there are eight electrodes on lead 102a, labeled $E_1$-$E_8$, and eight electrodes on lead 102b, labeled $E_9$-$E_{16}$, although the number of leads and electrodes is application specific and therefore can vary. For example, in some embodiments, thirty-two will be the preferred number of electrodes. The electrode array 110 is typically implanted along the dura of the spinal cord, and the IPG 100 generates electrical pulses that are delivered through the electrodes 106 to the nerve fibers within the spinal column. The IPG 100 itself is then typically implanted somewhat distantly in the buttocks of the patient, as is illustrated in FIG. 5.

As shown in FIG. 2, an IPG 100 typically includes an electronic substrate assembly 14 including a printed circuit board (PCB) 16, along with various electronic components 20, such as microprocessors, integrated circuits, and capacitors, mounted to the PCB 16. Ultimately, the electronic circuitry performs a therapeutic function, such as neurostimulation. A feedthrough assembly 24 routes the various electrode signals from the electronic substrate assembly 14 to the lead connectors 38a, 38b, which are in turn coupled to the leads 102 (see FIGS. 1A and 1B). The IPG 100 further comprises a header connector 36, which, among other things, houses the lead connectors 38a, 38b. The IPG 100 can further include a telemetry antenna or coil (not shown) for receipt and transmission of data to an external device such as a portable or hand-held or clinician programmer (not shown), which can be mounted within the header connector 36. Alternately, in some embodiments, charging coil 18 may be utilized as both a charging coil and a telemetry coil. As noted earlier, the IPG 100 usually also includes a power source, and in particular a rechargeable battery 26.

Also shown in FIG. 2 is an external charger 12 that is used to recharge the battery 26 in the IPG 100, which is explained in further detail below. The external charger 12 itself needs power to operate, and therefore may include its own battery 70, which may also be a battery that is rechargeable using a plug-in-the-wall holster ("cradle") or power cord connection much like a cellular telephone. Alternatively, the external charger 12 may lack a battery and instead draw its power directly from being plugged into a wall outlet (not shown).

The external charger 12 can contain one or more printed circuit boards 72, 74, which contain the circuitry 76 needed to implement its functionality. In one embodiment, and as shown in FIG. 2, most of the circuitry 76 can be located on an orthogonal circuit board 74, which reduces interference and heating that might be produced by the charging coil 17 positioned on circuit board 72, as is further explained in U.S. Patent Publ. No. 20080027500. The external charger 12 also consists of a case or housing 15, typically formed of a hard plastic, which may be divided into top and bottom portions 15a and 15b. The case 15 can be hand-held, or body-worn, or portable. Junction 13 illustrates the location where the top and bottom portions 15a and 15b may be snapped together or connected by other means. Clamps 19 may be utilized to hold the circuit boards 72 and 74 in place mechanically. Clamps 19 are shown formed as a part of the bottom case portion 15b, although this is not strictly necessary, as other means can be used to stabilize the components within the case 15.

To wirelessly transmit energy 29 between the external charger 12 and the IPG 100, and as shown in FIG. 2, the charger 12 typically includes an alternating current (AC) coil 17 that supplies energy 29 in the form of a magnetic field to a similar charging coil 18 located in or on the IPG 100 via inductive coupling. In this regard, the coil 17 within the external charger 12 is wrapped in a plane which preferably lies substantially parallel to the plane of the coil 18 within the IPG 100. Such a means of inductive energy transfer can occur transcutaneously, i.e., through the patient's tissue 25. The energy 29 received by the IPG's coil 18 can be rectified and used to recharge battery 26 in the IPG 100, which in turn powers the electronic circuitry that runs the IPG 100. Alternatively, the energy 29 received can be used to directly power the IPG's electronic circuitry, which may lack a battery altogether. The provision of charging field energy 29 may be controlled via the use of a power on/off button 80, e.g., located on the exterior of the case of the external charger.

Inductive charging between the two coils 17 and 18 can produce heating in the external charger 12. Because the external charger 12 is in proximity with the patient's tissue 25, there is a risk that the external charger 12 could overheat (or burn) the skin of the patient. This is especially true if a patient lies down while using the external charger. Lying down on the external charger can cause it to overheat and risks burning the patient. Moreover, a patient may fall asleep while laying down and charging. The inventor considers the most concerning position from a safety point of view to be when a patient is laying down on top of the charger (see, e.g., FIG. 6, position 251a). Lying down on top of the external charger, with the external charger in a "face down" position can completely insulate the external charger and put the patient's entire body weight against the external charger, causing it to reach a maximum safe temperature limit more quickly.

Techniques have been proposed for controlling external chargers to ensure that safe temperatures are not exceeded. For example, as explained in U.S. Patent Publ. No. 20110071597 ("the '597 Publication") which is incorporated herein by reference, the temperature of the external charger can be monitored by a thermocouple or thermistors. Should a threshold temperature be exceeded (Tmax), generation of the magnetic charging field at the external charger may be temporarily suspended, or the intensity of the magnetic field may be reduced, to allow the external charger time to cool. At some later point, perhaps once the temperature falls a few degrees below Tmax (i.e., to Tmin), charging can once again be enabled or restored to its original intensity level, with the process essentially duty cycling the charging coil 17 in external charger on and off, as shown in FIG. 3.

Other prior art solutions, such as those explained in U.S. Patent Publ. No. 20110178576 ("the '576 Publication") which is incorporated herein by reference, have been proposed in which charging is at least partially controlled based on a sensed pressure (i.e., force) impingent on its case. This pressure may be indicative of the pressure between the external charger and a patient's tissue. Such an external charger may include pressure detection circuitry coupled to one or more pressure sensors for controlling the external charger in accordance with the sensed impingent pressure. The sensed pressure can then be used to control charging, for example, by suspending charging, by reducing the intensity, by adjusting a maximum set point temperature for the external charger based on the measured pressure, or by issuing an alert via a suitable user interface.

Despite such solutions, the inventor considers that further improvements can be made to the safety of external charger technology, and this disclosure provides solutions, in which an external charger is controlled based on determining the position of the external charger, e.g., in three-dimensional space.

BRIEF DESCRIPTION OF THE DRAWINGS

FIG. 4 shows an embodiment of an improved external charger, which includes a position determination element and associated position detection circuitry.

DETAILED DESCRIPTION

As is explained more fully in the '576 Publication, heat transfer between an external charger and a patient's tissue may increase as the pressure between the two is increased. As a result, an external charger at a given temperature will transfer more heat—and thus will feel hotter—to a patient as the pressure is increased. This is significant when one realizes that an external charger is often held or pressed firmly against the patient's skin. For example, an external charger for an IPG is often placed in a retaining belt or "fanny pack," or integrated in other structures such as mattress pads, that the patient may lean against or lie upon, and which would tend to press the external charger against the patient. Additionally, if a user lies on the external charger, it establishes a thermally well-insulated environment that traps the heat generated by the charging process.

To address these realities, an improved external charger for an implantable medical device is disclosed in which charging is at least partially controlled based on a determined position of the external charger, e.g., in three-dimensional space, which determined position is likely indicative of the pressure between the external charger and a patient's tissue. The improved external charger includes at least one position detection element and circuitry coupled thereto for controlling the external device in accordance with the determined position. The determined position can be used to control charging, for example, by adjusting the intensity of the magnetic field, by suspending charging, by adjusting a maximum set point temperature for the external charger based on the determined position, or by issuing an alert via a suitable user interface. By so controlling the external charger on the basis of the determined position, the external charger is less likely to create potentially problematic or uncomfortable conditions for the user.

Figure 1:
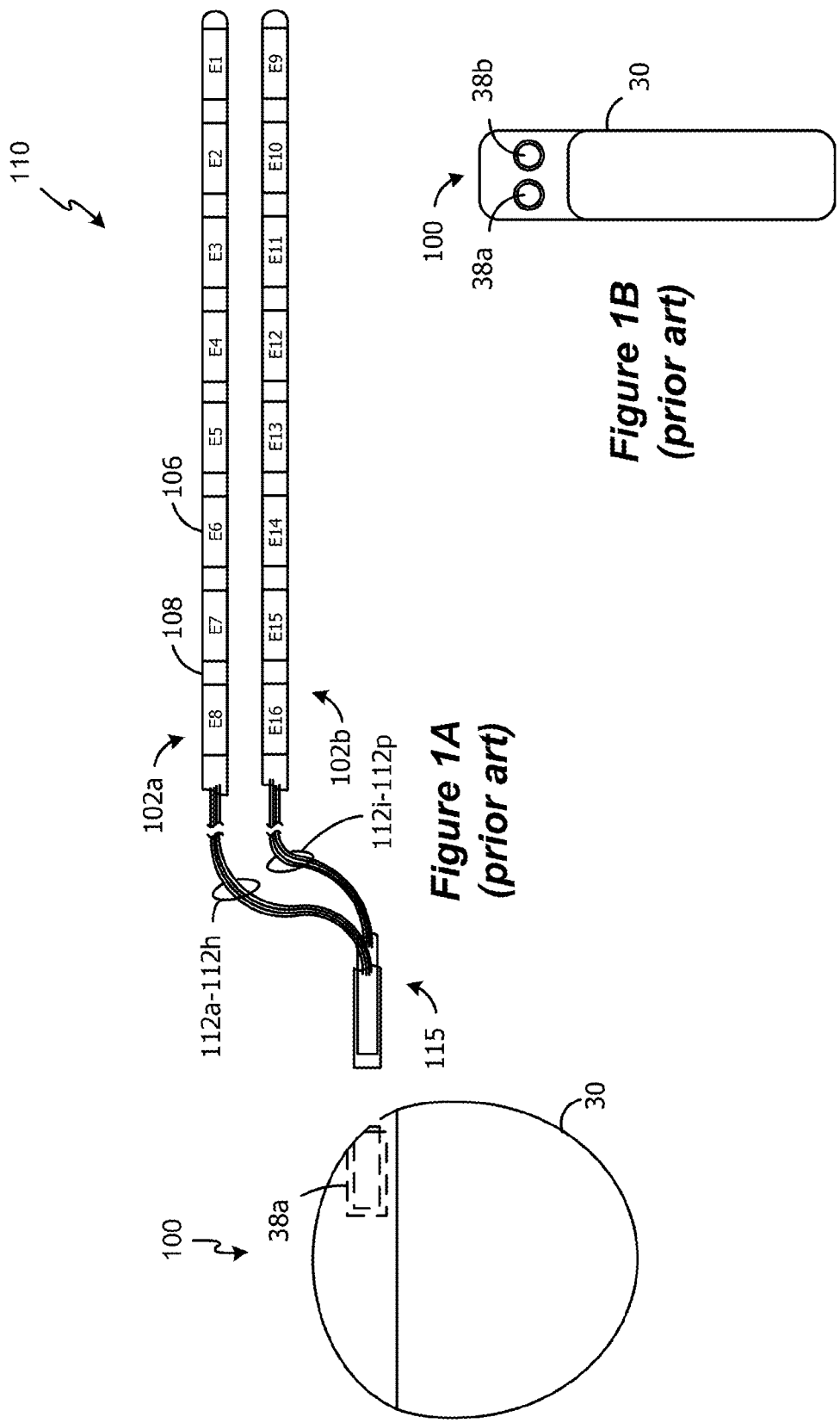
FIGS. 1A and 1B show an implantable pulse generator (IPG), and the manner in which an electrode array is coupled to the IPG, in accordance with the prior art.
Figure 2:
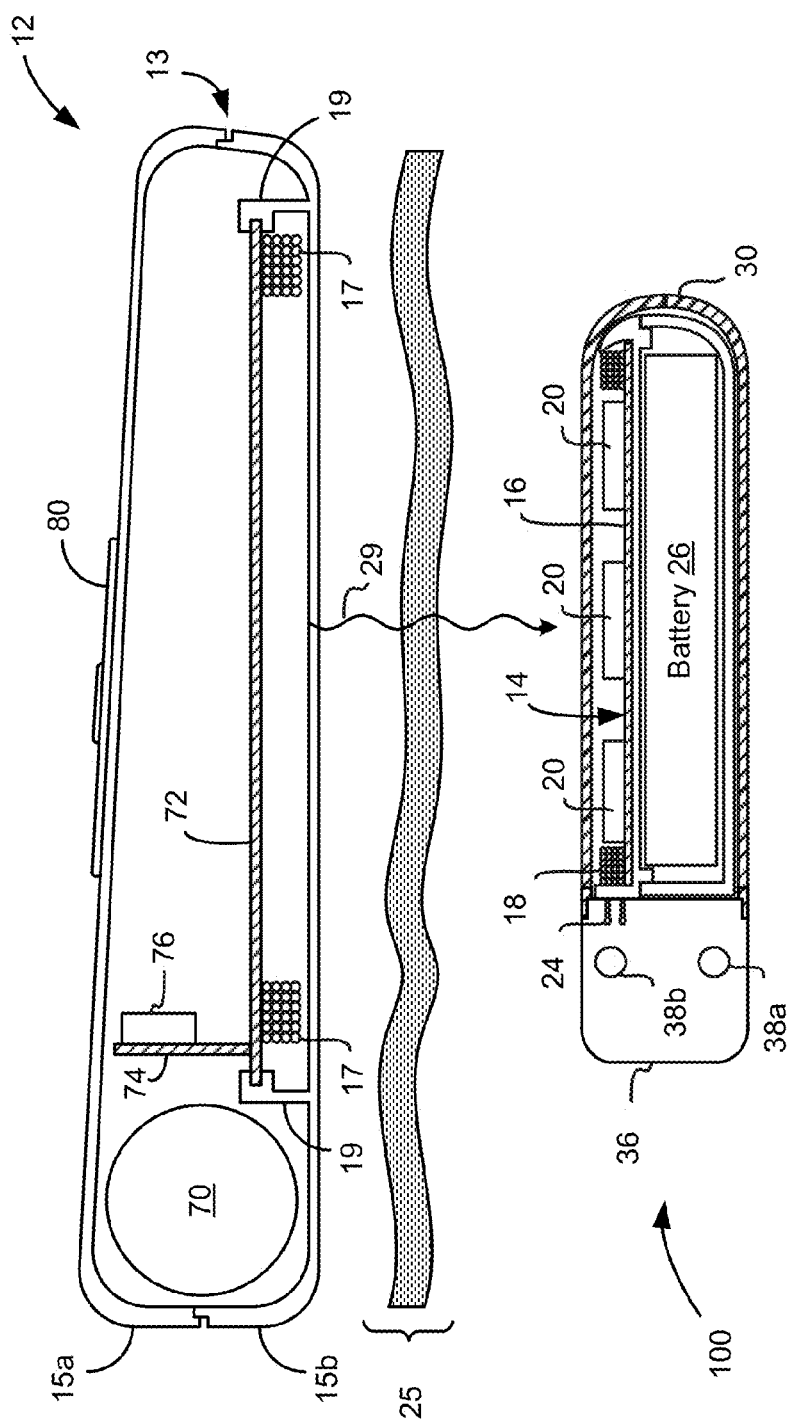
FIG. 2 shows the IPG in relation to an external charger, in accordance with the prior art.

FIG. 4 shows an embodiment of the improved external charger 200. Many of the components in improved external charger 200 are the same as those appearing in the prior art charger 12 of FIG. 2, and, for simplicity, such components are not described again in detail. Newly-added to the external charger 200 is a position determination element 77 for transmitting information relating to the position of the external charger to external charger control circuitry 76. Position determination element 77 may comprise an accelerometer, e.g., a microelectromechanical systems (MEMS) accelerometer, such as an ultra-compact low-power three-axes linear accelerometer. An accelerometer may include a sensing element and an integrated circuit (IC) interface able to provide the measured acceleration of the device through a serial interface. Acceleration measurements reported by the accelerometer may take the form of electrical measurements indicative of the relative pull of gravity on the device along its three primary axes. The position determination element 77 may comprise, for example, part number ADXL346, manufactured by Analog Devices, Inc. Other types of position determination elements 77 may also be used, such as six-axis gyrometers. Also newly-added to the external charger 200 in FIG. 4 is pressure sensing element 170 and temperature sensing element 162. As discussed more fully in the '576 Publication, the pressure sensing element 170 may comprise a force sensor that, for example, outputs a varying resistance proportional to the force applied to the sensor, or it may comprise a strain gauge. As discussed more fully in the above-reference '597 Publication, the temperature sensing element 162 may comprise, for example, a thermistor or thermocouple. The locations of pressure sensing element 170 and temperature sensing element 162 affixed to the printed circuit board (PCB) 72 in FIG. 4 are not meant to be limiting in any way; rather, affixing these elements to PCB 72 is just one exemplary location where such elements may be included in the improved external charger 200.

As shown in FIG. 4, the external charger 200 has a case 15 that is substantially planar in design as is typical, meaning that case 15 can be confined to a plane 99 substantially parallel with one of its major surfaces. Such substantially planar shape for the case 15 facilitates placing the external charger 200 against the skin of a patient, as already mentioned. When the patient is lying on top of the external charger, an external pressure is exerted on the case of the external charger and is oftentimes substantially orthogonal to plane 99 of the external charger 200. As shown, position determination element 77 is affixed to one side of the PCB 72 and communicates position information to a microcontroller 160 (FIG. 7A) in the external charger 200.

Figure 5:
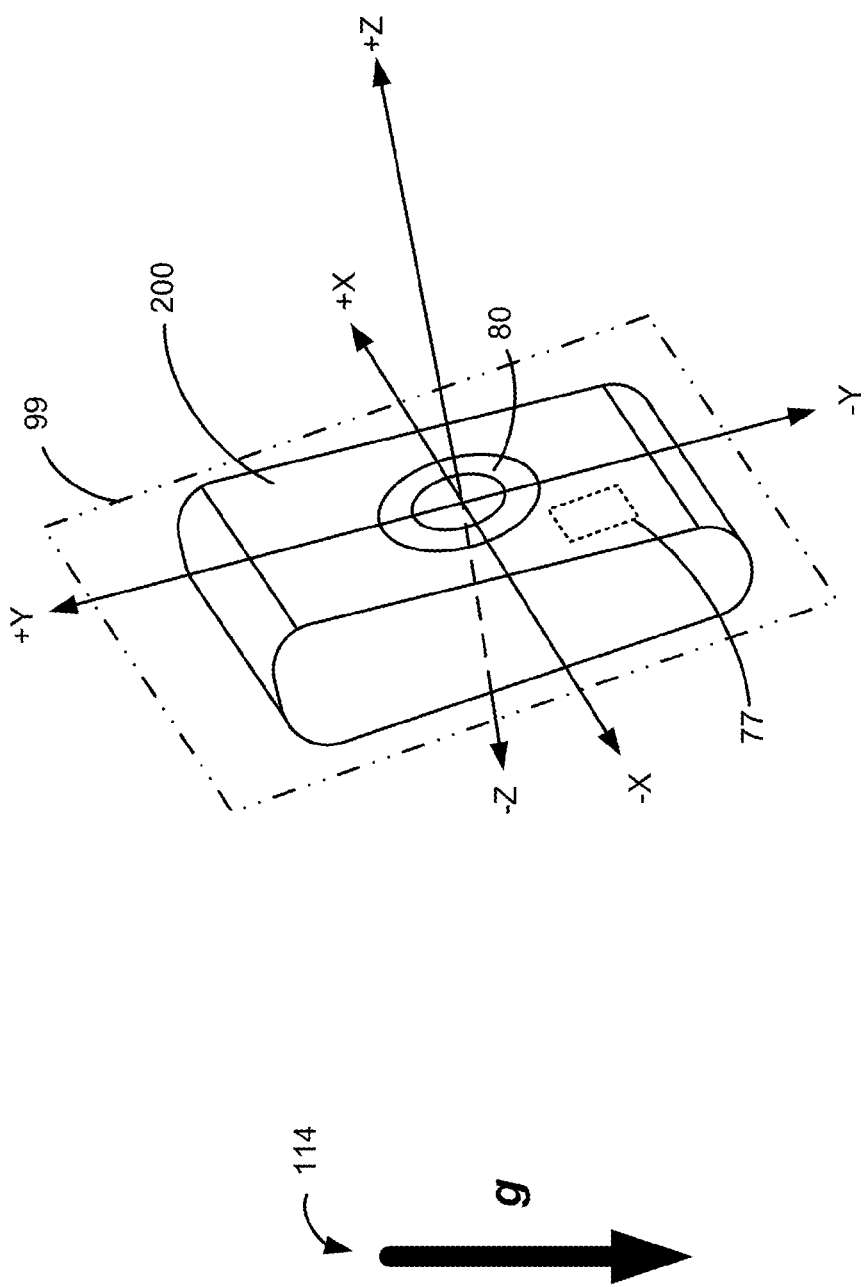
FIG. 5 shows an embodiment of an improved external charger including a position determination element and associated position detection circuitry, along with a vector representative of gravity and the three primary axes of the external charger.

FIG. 5 shows the improved external charger 200 with the accelerometer 77 and associated position detection circuitry, along with a vector 114 labeled 'g' that is representative of a gravity vector. Also shown in FIG. 5 are the three primary axes of the external charger (X, Y, and, Z). As shown in FIG. 5, the x-axis of external charger 200 lies parallel to the shorter edge of the external charger 200, with positive x values to the right side (as shown in FIG. 5) and negative values to the left side. Likewise, the y-axis lies parallel to the longer edge of the external charger 200, with positive y values to the top side (as shown in FIG. 5) and negative values to the bottom side. Finally, the z-axis extends outwardly from the external charger 200, i.e., normal to plane 99, with positive z values to the side of the device having the power on/off button 80 and negative values to the back side of the external charger 200, i.e., the side of the external charger that is applied to the user when the external charger is charging. The axial directions and orientations shown in FIG. 5 are merely exemplary and are used so that directions may be referred to consistently throughout this application.

As shown in FIG. 5, the accelerometer 77 may return positional data indicating that the majority of the force of gravity is acting in the negative y-axis direction of external charger 200. As shown in FIG. 5, comparatively smaller components of the gravity vector would be acting in the negative x and negative z directions. For the sake of explanation, if the external charger 200 were instead lying with power on/off button 80 face down on a flat surface such as a table or mattress, the exemplary accelerometer may return positional data indicating that 100% of the force of gravity was acting in the positive z-axis direction. No matter which direction the external charger device is oriented, the direction of gravitational pull remains towards the center of the Earth.

As mentioned above, certain external charger positional orientations are indicative of potentially hazardous charging conditions for the patient. For example, if the external charger is in the "face down" position, i.e., with 100% of the force of gravity acting in the positive z-axis direction, it is likely that the patient is lying down on top of the charger, such as on a bed or other horizontal surface. Due to the risk of injury or discomfort to the patient caused by the external charger overheating when in such a fully-insulated and "face down" position, such a position may be deemed to be in a "critical position." As used herein, a critical position refers to an external charger position or range of positions in which there is an increased likelihood of harm or discomfort to the patient. For example, in one particular embodiment, a critical position will be any position wherein a substantial amount, e.g., 50% or more of the force of the gravity vector, is aligned in the positive z-axis direction (as oriented in FIG. 5), i.e., a substantially "face down" position.

In other embodiments, there may be a plurality of ranges of device positions of varying degrees of criticality. In one embodiment, a first, i.e., "least critical," position may be one in which 0-50% of the gravity vector is acting along the external charger device's positive z-axis; a second, i.e., "more critical," position may be one in which 50-85% of the gravity vector is acting along the external charger device's positive z-axis; and a third, i.e., "most critical" position may be one in which 85-100% of the gravity vector is acting along the positive z-axis of the external charger.

The position-determining external charger 200 according to the teachings presented herein is thus able to control charging behavior according to the particular position that the external charger is oriented in. For example, as the criticality of the position of the external charger increases, the intensity of the magnetic field produced by the charger may be decreased, or the temperature set point maximum may be lowered, and/or the duration of time before charging is automatically suspended may be decreased. Likewise, user alerts of increasing severity levels may be presented to the user as the positional criticality increases. In other embodiments, there may be more than three discrete critical position ranges, or there may be a smooth continuum of critical positions, where the intensity, temperature set point maximum, and/or the charging duration is calculated for any possible device position, e.g., as a function of the percentage of the gravity vector acting in the positive z-axis direction (as oriented in FIG. 5).

Figure 6:
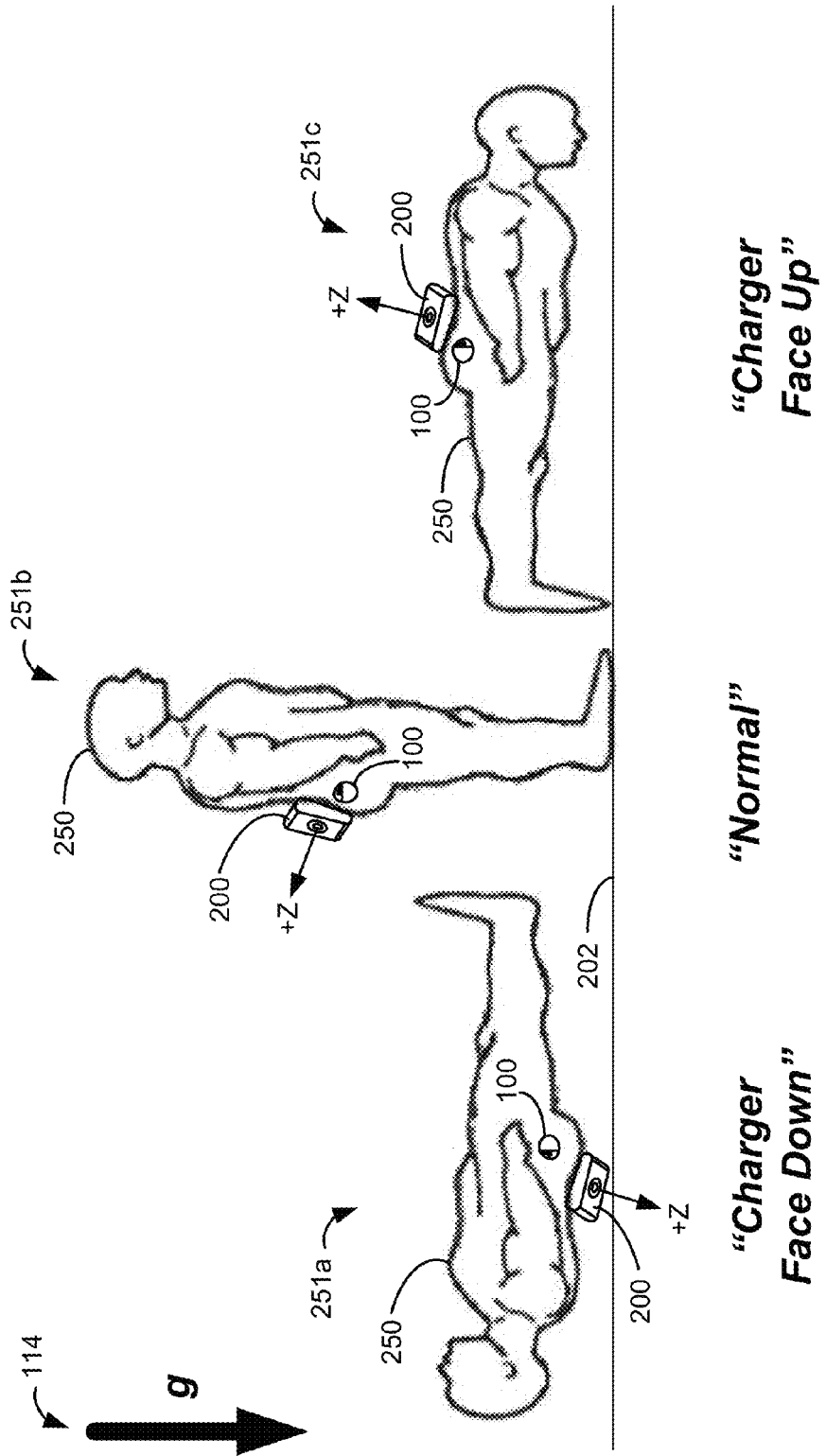
FIG. 6 shows several typical body positions of a patient while using an external charger.

FIG. 6 shows several typical body positions 251 of a patient 250 while using an external charger 200. Patient 250 is illustrated in FIG. 6 as lying down on top of external charger 200 with external charger 200 in the "face down" position 251 a. In this position 251 a, and given the backside location of the IPG 100, there may be pressure on the external charger 200 because the patient 250 might be lying on top of external charger 200. Gravity vector 114 in this position 251a is acting substantially in the positive z-axis direction of external charger 200, and thus, according to one embodiment, external charger 200 would be deemed to be in a critical position. In such a critical position, the external charger 200 is at a higher risk of overheating due to it being fully-insulated by the body of patient 250 and flat surface 202.

If patient 250 were to rise to his feet, he would be in position 251b, such that external charger 200 is in a "normal" charging position. A negligible percentage of the gravity vector 114 is acting in the positive z-axis direction of external charger 200. Thus, external charger 200 would be deemed to be in a non-critical position. In such a non-critical position, the charging algorithm of the external charger could follow default or other user-programmed charging routines.

Finally, if patient 250 were to lie back down on his stomach, he would be in position 251c, with external charger 200 in a "face up" charging position. In this position 251c, the gravity vector 114 is not acting in the positive z-axis direction of external charger 200; in fact, it's acting substantially in the negative z-axis direction. Thus, the external charger 200 would again be deemed to be in a non-critical position. This position 251c is substantially safer than the "face down" position 251a because the patient's body weight will not be pressing against the external charger 200, and the top of the charger will likely be open to ambient air and not insulated.

Figure 7A:
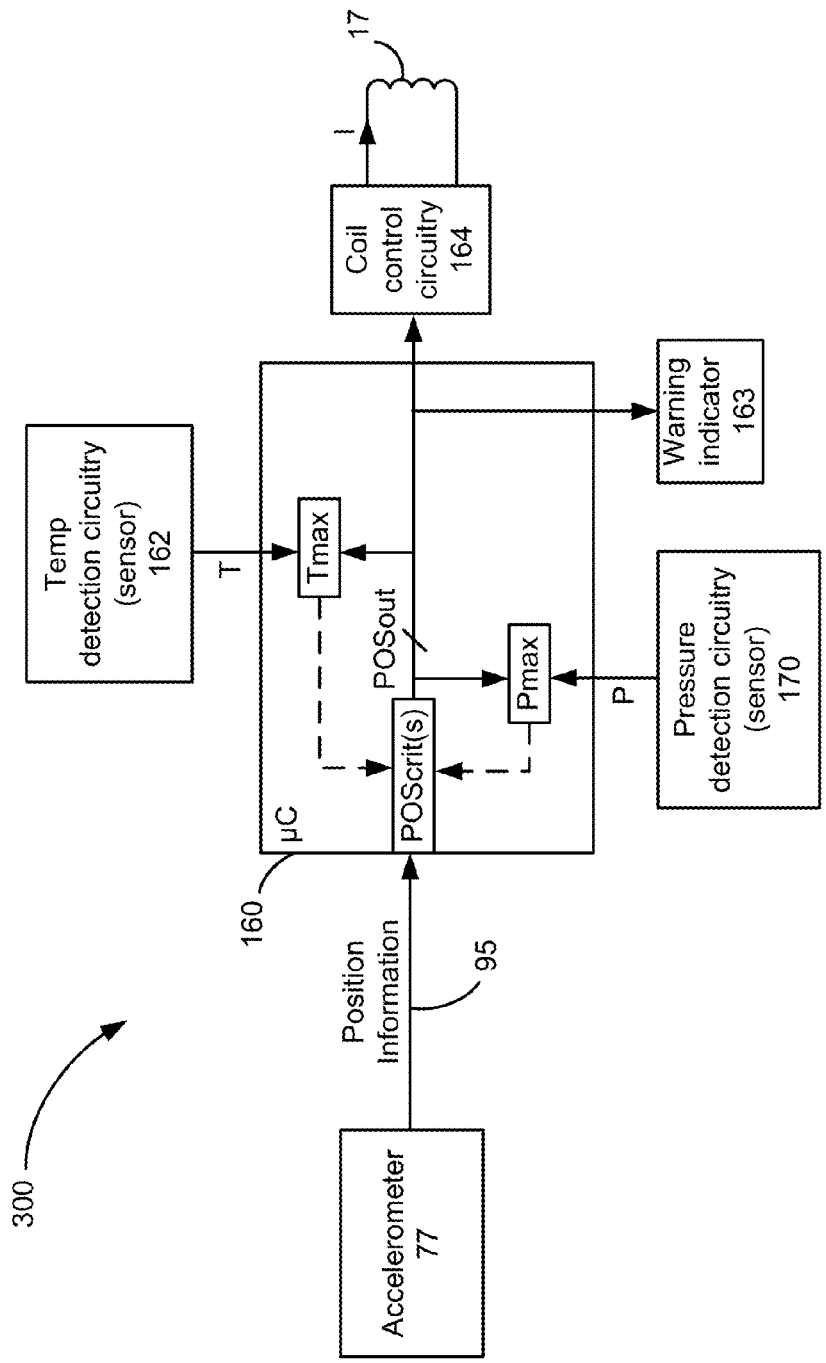
FIG. 7A shows an embodiment of circuitry for controlling the external charger of FIGS. 4 and 5 as a function of determined external charger position.

FIG. 7A shows an example of control circuitry 300 useable in the external charger 200 for detecting when the external charger is oriented in a critical position. In the example shown, the position determination element (e.g., accelerometer 77) comprises a small, thin, ultra-low power, 3-axis accelerometer that provides high resolution (e.g., 13-bit) position information 95 to the external charger 200's microcontroller 160. The position information 95 may be formatted as, e.g., 16-bit two's complement numbers (thus providing for the encoding of both positive and negative values), and may be accessible through either an SPI (3- or 4-wire) or $I^2C$ digital interface.

Microcontroller 160 preferably has access to values in memory corresponding to a range of critical position(s) (i.e., "POScrit(s)") for the external charger. For example, POScrit1 may correspond to the threshold amount of the gravity vector permitted to be in the external charger's positive z-axis direction, below which the external charger is deemed to be in a least critical position; POScrit 2 may correspond to a higher positive z-axis threshold, such that positive z-axis values between POScrit1 and POScrit2 are deemed to be in a more critical position; and so forth for as many different discrete ranges of critical positions desired that the external charger 200 discern.

By comparing the positional information 95 returned by accelerometer 77 to the POScrit values stored in memory, microcontroller 160 generates an output, POSout, which may be a single digital signal or a bus of signals. For example, if the POScrit1 value has not been exceeded, POSout may be set to '0'; if the POScrit1 value (but not the POScrit2 value) has been exceeded, POSout may be set to '1'; and if the POScrit2 value has been exceeded (but not the POScrit3 value), POSout may be set to '2,' etc. In this way, the value of POSout is indicative of the criticality level of the current position of the external charger. In a simpler embodiment, there may be only a single POScrit value stored in memory, such that POSout provides only a binary output, i.e., POSout='0' for a non-critical position, and '1' for a critical position.

The POScrit values would normally be set and stored in the microcontroller 160 by the manufacturer, but these values could also be programmable into the external charger 200 by the patient or clinician based on patient experience using the user interface of the charger.

Microcontroller 160 can record position information 95 as a function of time, and set POSout accordingly, which can allow for more sophisticated external charger 200 control. For example, if the position information 95 indicates that the external charger 200 is in a critical position (POSout>'0') for only a short (e.g., less than a minute or so) or sporadic period of time (e.g., occurring only a few times a minute), it may be unnecessary to take POSout to a value indicating criticality.

Figure 3:
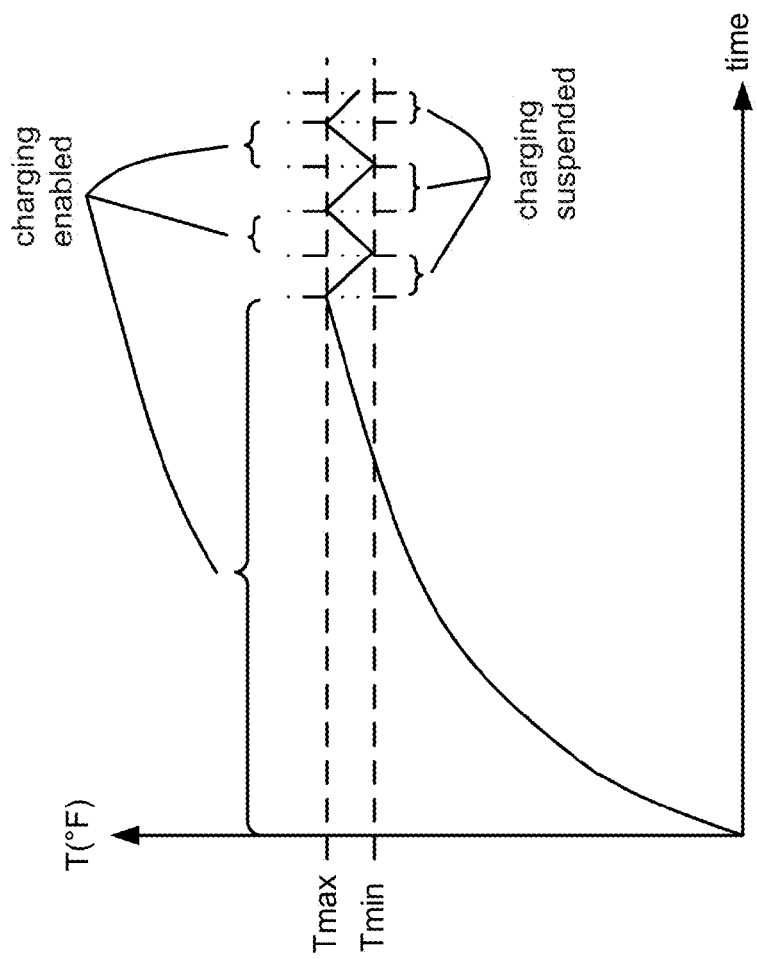
FIG. 3 shows regulation of the external charger's temperature during IPG battery charging, in accordance with the prior art.
Figure 7B:
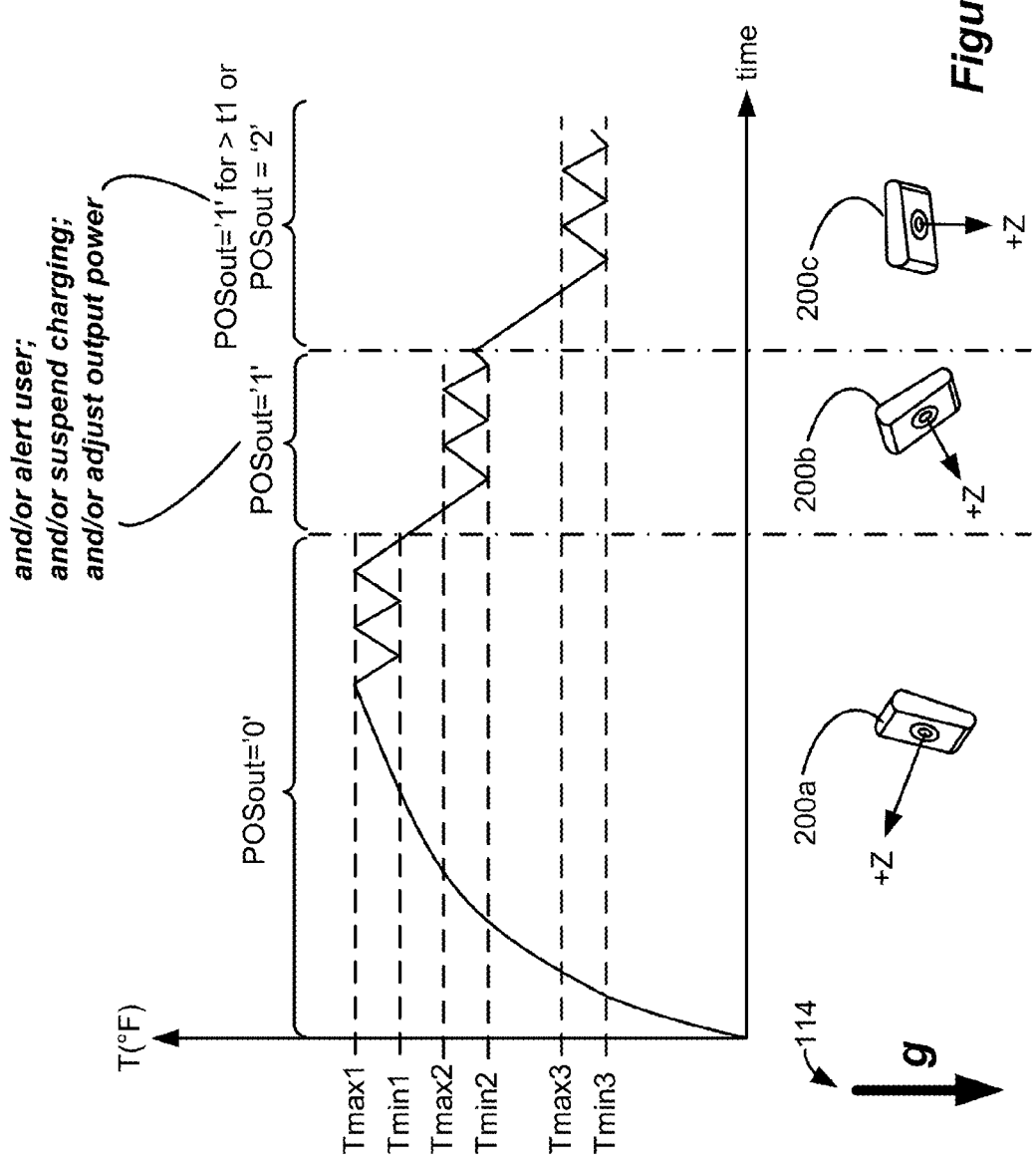
FIG. 7B shows control of the temperature of the external charger of FIGS. 4 and 5 as a function of determined external charger position in three-dimensional space.

POSout can be used in different way to control the external charger 160. For example, POSout can be used to set the maximum temperature, Tmax, allowable by the external charger 200, as disclosed in the above-referenced '597 Publication. For example, and as shown in FIG. 7B, as POSout increases over time (from POSout='0' to '1' to '2'), Tmax can be lowered (from Tmax1 to Tmax2 to Tmax3). (Tmin values can also likewise be lowered to allow proper duty cycling of the external charger, as explained earlier with reference to FIG. 3). In this way, as the position of the external charger 200 becomes more critical—i.e. more likely to be thermally insulated and/or pressed against the patient, Tmax is lowered so that the external charger 200 runs cooler. Tmax can also be lowered as positions of criticality are experienced for longer periods of time. For example, and as also shown in FIG. 7B, Tmax can be lowered to Tmax3 if POSout='1' for an extended period of time (>t1). In another alternative, should POSout indicate a position of criticality, charging can be temporarily suspended until the critical position is alleviated. This can occur by coil control circuitry 164 disabling the charging coil 17 (i.e., setting the AC charging current though the charging coil, I, equal to 0). Further details concerning the temperature detection circuitry 162 used to indicate the temperature T of the external charger 200 to the microcontroller 160, the use of Tmax to control charging, etc., are explained in the '597 Publication, and so such further details are not explained here.

Tmax can also be used by the microcontroller 160 to control POSout, as shown in the dashed line in FIG. 7A. For example, if Tmax is already set to a relatively high value, the microcontroller 160 may be more concerned if the positional information 95 indicates criticality of position, and so may issue POSout='1' (or '2', etc.) sooner. In other words, Tmax may be used to set the POScrit(s) threshold to lower levels if Tmax is relatively high, or to increase those thresholds if Tmax is relatively low.

POSout can also be used to trigger a warning indicator 163 comprising part of the user interface of the external charger 200. For example, as POSout increases, an audible alarm may issue from the warning indicator, which in this example could comprise a speaker. The volume or pitch of the alarm may be changed depending on the criticality of the position. Other user alarms may be visual or tactile in nature. For example, the warning indicator 163 could comprise light or a display, or a vibratory motor. Regardless of the form taken, such alarms issuing from the warning indicator 163 can draw the user's attention to the potentially critical position of the external charger 200 so that the user can change position if possible.

POSout can also be used to control the intensity of the magnetic field external charger 200. Thus, POSout is in FIG. 7A also sent to coil control circuitry 164, which can control the AC charging current though the charging coil (I) appropriately. For example, if POSout='0', I can be set by the coil control circuitry 164 to a maximum value; if POSout='1', I can be lowered, etc. In this way, as the position of the external charger 200 becomes more critical, I is lowered to reduce the intensity of the magnetic field. This will lower the temperature of the external charger 200, thus improving patient safety and comfort, and alleviating consequences brought on by critical external charger 200 positions. It should be noted that coil control circuitry 164 can be used to control charging current I for other reasons as well. For example, in a closed-loop charging system, current I can be controlled in accordance with the degree of coupling between the external charger 200 and the IPG 100.

The various disclosed means of using POSout to control the external charger 200 can also be used together, and are not mutually exclusive. For example, upon sensing a critical position, Tmax can be lowered, and an alarm could issue form the warning indicator 163. Or Tmax can be lowered, and then an alarm issued after some period of time. Or, Tmax could be lowered along with the intensity, etc. POSout can also be used to control the external charger 200 in other ways. For example, POSout could be used to control or select a particular charging algorithm or program operating in the external charger 200. Furthermore, POSout need not be limited to the ultimate control of the external charger 200's temperature, and could be used for other reasons as well, some of which are discussed further below.

Position information 95 provided by the accelerometer 77 can also be used to modify other means of external charger 200 control. Referring again to FIG. 7A, the depicted external charger 200 also contains means for control based on detected pressure impingent pressure, as was described in the above-referenced '576 Publication. Pressure detection circuitry 170 provides information about the impingent pressure, P, to the microcontroller 160, which can compare the sensed pressure to a threshold Pmax and control charging accordingly. Adding position criticality to such pressure-based means of control adds additional sophistication to external charger control. For example, if POSout indicates a position of criticality, but the sensed pressure P is low, the microcontroller 160 may determine that although the position suggests that the external charger 200 may be positioned under the patient, the lack of pressure does not truly create a critical condition for the user. Thus, POSout might, in this circumstance, be overridden by the detected pressure, and thus the microcontroller 160 would continue allowing charging at relatively high temperatures or intensities. POSout may also be used to adjust Pmax, such that Pmax is lowered during times of position criticality, and raised during times when position is not deemed critical.

To this point in the disclosure, it has been assumed that POSout is quantized into discrete values in accordance with various external charger position ranges. However, this is not strictly necessary, and control of the external charger 200 can occur in a more analog fashion, such that various parameters (Tmax, Pmax, I, alarm volume, etc.) are controlled in a smooth fashion in response to the position information 95. In such an embodiment, strict POScrit thresholds might not be necessary or used at all.

Figure 8:
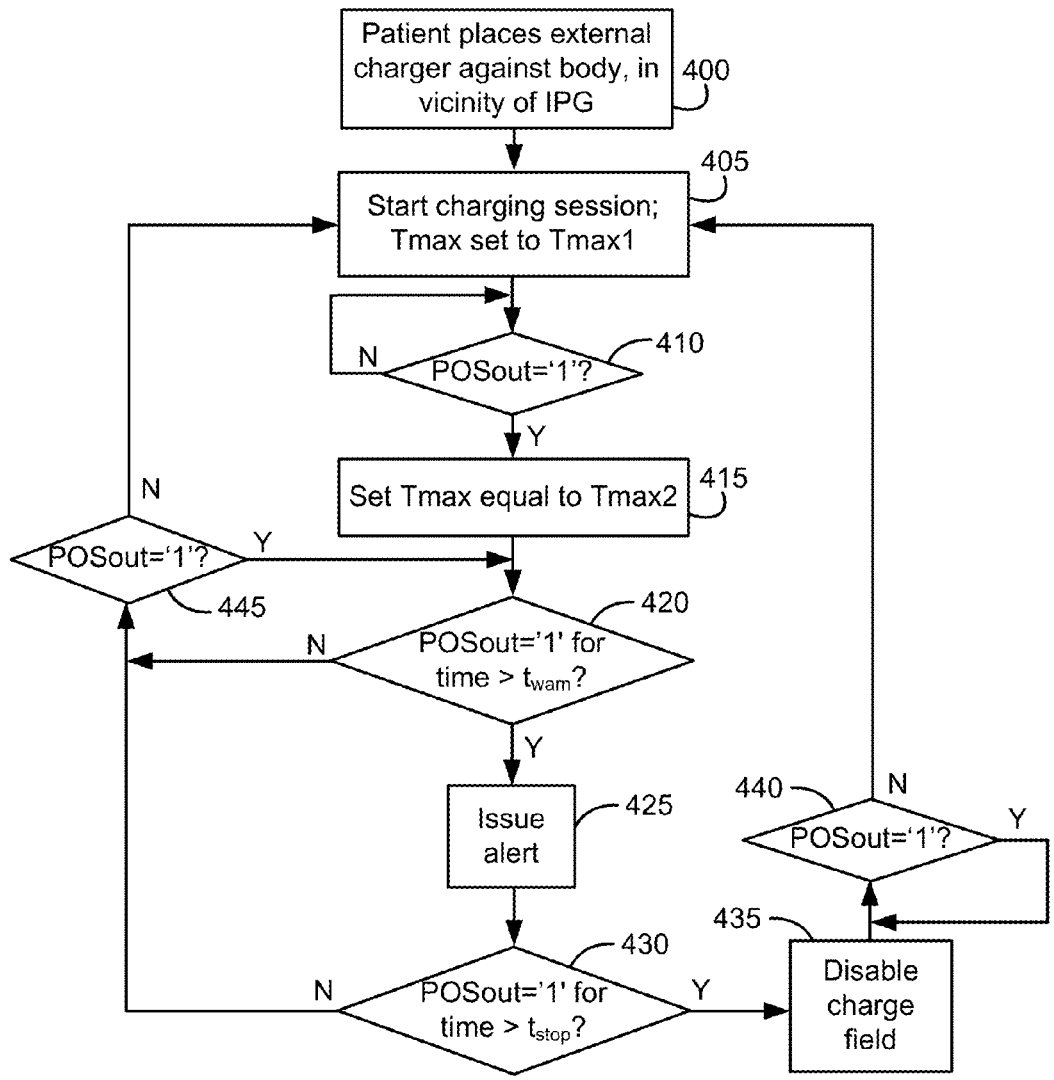
FIG. 8 shows a flow chart of one exemplary method for controlling an external charger as a function of determined external charger position.

FIG. 8 is a flow chart detailing one exemplary process for using control circuitry 300 to control charging based on the determined position of an external charger. In this example, control is based on whether the external charger has been determined to be oriented in a single critical position, i.e., whether POSout has been set to '1.'

After the patient places the external charger against their body in the vicinity of the IPG 100 (Step 400), the patient can start a charging session using the user interface of the external charger (Step 405). At this point, the external charger may also set the maximum temperature to a relatively high maximum temperature set point value, Tmax1, and so may duty cycle the generation of the produced charging field to maintain that temperature as discussed earlier. During the charging session, microcontroller 160 continually (or periodically, e.g., at specified time intervals) monitors in the position of the external charger 200 to determine whether the device is in a critical position, i.e., whether POSout='1' (Step 410). If not, the external charger 200 continues to provide power to the IPG 100 as normal, and as subject to other traditional considerations such as the fullness of the IPG's battery 26. If, instead, the external charger 200 is in a critical position, i.e., POSout='1', microcontroller 160 may then set the maximum temperature to a new lower set point value, Tmax2, less likely to discomfort the patient (Step 415).

Next, microcontroller 160 determines whether the external charger has been in a critical position, i.e., POSout='1', for greater than a predetermined critical amount of time, $t_{warn}$, e.g., 15 minutes (Step 420). If not, the external charger 200 may continue to provide power to the IPG 100 as normal, and can reset the maximum temperature set point back to the higher Tmax1 should the external charger later return to a non-critical position, i.e., if POScrit ='0' (Steps 445 and 405). If $t_{alarm}$ is exceeded, the microcontroller 160 may issue an alert to the user via the warning indicator 163 in any of the abovementioned ways, such by visual, auditory, or tactile feedback suitable for interpretation by the user of the external charger (Step 425).

After issuance of the alert, the microcontroller 160 assesses whether the position of the external charger has been critical for an even greater predetermined amount of time, $t_{stop}$, e.g., 30 minutes. If not, the external charger 200 may continue to provide power to the IPG 100 as normal and can reset the maximum temperature set point back to the higher Tmax1 should the external charger later return to a non-critical position (Steps 445 and 405). If the external charger has been in a critical position for greater than $t_{stop}$, the microcontroller 160 may suspend the wireless transmission of power during the charging session, e.g., by disabling the external charger's charge coil 17 (Step 435). The external charger may remain suspended until the external charger is reoriented such that POSout is set to '0' (Step 440). Once this occurs, the charger may resume the wireless transmission of power during the charging session with Tmax set to Tmax1 (Step 405).

Because the external charger is often placed against a patient's back or buttocks, it can be difficult for the patient to receive alert information from the external charger. To provide better alert feedback to the patient, the external charger may optionally transmit alert information (e.g., Step 425) via a suitable communications link to another external device, e.g., a remote control or external controller. Such additional external devices may then indicate any potentially unsafe conditions to the patient. This type of communication is disclosed in commonly-owned U.S. Patent Publ. No. 20100305663 ("the '663 Publication"), filed Jun. 2, 2009. An alert may comprise the severity level of the external charger's position as reported by the position detection circuitry, or a simple indication that the external charger is in a critical position and/or for how long.

Although it is envisioned that the disclosed external charger 200 would normally be used to charge or recharge a battery 26 within the IPG 100, the external charger 200 can also be used with IPGs or other implantable medical devices that lack a battery. This could occur for example in a system in which the IPG continually wirelessly receives energy from the external charger 200, which IPG in turn rectifies and uses this energy without storage.

Although a primary feature of this disclosure is the use of position determination to regulate the generated heat of the external charger, it should be noted that position in three-dimensional space can be used to control the external charger in other more generic fashions. As already noted, position can be used to suspend or diminish charging or to issue a warning, which features are useful even if temperature control is not an issue. For example, it might be warranted to issue an alert or to suspend operation when the external charger is in a particular position merely because putting pressure on the external device when oriented in such a way may physically hurt the patient or damage the external charger. Position determinations can be used to control the external charger in other ways too, such as by automatically generating a charging field (i.e., turning the charger on) when the detected position indicates that the external charger is likely in a proper position to charge the implant. In such an application, it may be useful to program the external charger with positional information regarding the expected corresponding position of the implant.

Although discussed in the context of an external charger, it should be understood that detection of position may also be used to control other sorts of devices in an implantable medical system. For example, position determination can be used to similarly control an external controller which wirelessly transmits instructions used to program the implantable medical device or to wirelessly read status information therefrom, such as disclosed in used in the above-referenced '663 Publication.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An external charger for an implantable medical device, comprising:
   a coil for wirelessly providing power to the implantable medical device;
   at least one position determination element for determining an orientation of the external charger in three-dimensional space relative to a gravity vector; and
   control circuitry coupled to the at least one position determination element for controlling the external charger in accordance with the determined orientation.

2. The external charger of claim 1, wherein controlling the external charger in accordance with the determined orientation further comprises controlling the power in accordance with the determined orientation.

3. The external charger of claim 2, further comprising a temperature sensor for sensing a temperature of the external charger, wherein the control circuitry additionally controls the power in accordance with the sensed temperature.

4. The external charger of claim 2, further comprising a pressure sensor for sensing a pressure of the external charger, wherein the control circuitry additionally controls the power in accordance with the sensed pressure.

5. The external charger of claim 2, wherein the control circuitry controls the power in accordance with the determined orientation by adjusting a temperature set point for the external charger.

6. The external charger of claim 1, further comprising a warning indicator, wherein the warning indicator issues an alert in accordance with the determined orientation.

7. The external charger of claim 2, wherein the control circuitry controls the power in accordance with the determined orientation by disabling the coil.

8. The external charger of claim 2, wherein the control circuitry controls the power in accordance with the determined orientation by modifying an intensity of the power.

9. The external charger of claim 8, wherein the intensity is modified by modifying a current of the coil.

10. The external charger of claim 1, further comprising a case for housing the coil, the at least one position determination element, and the control circuitry.

11. The external charger of claim 10, wherein the at least one position determination element is mounted to a printed circuit board within the case.

12. The external charger of claim 2, wherein the control circuitry further determines whether the determined orientation corresponds to at least one critical orientation programmed into the external charger.

13. The external charger of claim 12, wherein the at least one critical orientation comprises at least one orientation wherein the external charger is substantially face down.

14. The external charger of claim 12, wherein the control circuitry further controls the power when it is determined to be in the critical orientation for a period of time.

15. The external charger of claim 2, wherein the control circuitry compares the determined orientation to a plurality of orientation ranges, and wherein the control circuitry controlling the power in accordance with one of the orientation ranges corresponding to the determined orientation.

16. The external charger of claim 1, wherein the control circuitry comprises a microcontroller.

17. The external charger of claim 1, wherein the at least one position determination element comprises an accelerometer or gyrometer.

18. The external charger of claim 1, wherein the determined orientation is likely indicative of a pressure between the external charger and a patient's tissue.

19. The external charger of claim 2, wherein controlling the power in accordance with the determined orientation comprises automatically generating a charging field using the coil when the determined orientation is a proper orientation for providing power to the implantable medical device.

20. A system, comprising:
    an external device, comprising:
       a coil for providing a wireless transmission,
       at least one position determination element for determining an orientation in three-dimensional space of the external device relative to a gravity vector, and
       control circuitry coupled to the at least one position determination element for controlling the external device in accordance with the determined orientation; and
    an implantable medical device for receiving the wireless transmission from the external device.

21. The system of claim 20, wherein the external device further comprises a temperature sensor for sensing a temperature of the external device, wherein the control circuitry additionally controls the external device in accordance with the sensed temperature.

22. The system of claim 20, wherein the external device further comprises a pressure sensor for sensing a pressure of the external device, wherein the control circuitry additionally controls the external device in accordance with the sensed pressure.

23. The system of claim 20, wherein the control circuitry controls the external device in accordance with the determined orientation by adjusting a temperature set point for the external device.

24. The system of claim 20, wherein the control circuitry controls the external device in accordance with the determined orientation by issuing an alert.

25. The system of claim 20, wherein the control circuitry controls the external device in accordance with the determined orientation by disabling the coil.

26. The system of claim 20, wherein the control circuitry controls the external device in accordance with the determined orientation by modifying an intensity of the wireless transmission.

27. The system of claim 20, wherein the at least one position determination element comprises an accelerometer or gyrometer.

28. The system of claim 20, wherein the control circuitry further determines whether the determined orientation corresponds to at least one critical orientation programmed into the external device.

29. The system of claim 28, wherein the control circuitry controls the external device when it is determined to be in the critical orientation for a period of time.

30. The system of claim 20, wherein the control circuitry compares the determined orientation to a plurality of orientation ranges, and wherein the control circuitry controls the external device in accordance with one of the orientation ranges corresponding to the determined orientation.

31. The system of claim 20, wherein the determined orientation is likely indicative of a pressure between the external device and a patient's tissue.

32. The system of claim 20, wherein the control circuitry comprises circuitry to automatically provide the wireless transmission using the coil when the determined orientation is a proper orientation for providing the wireless transmission.

33. A method for operating an external charger, comprising:
- enabling the external charger to wirelessly transmit power to an implanted medical device during a charging session;
- determining an orientation of the external charger in three-dimensional space relative to a gravity vector during the charging session; and
- controlling the external charger during the charging session in accordance with the determined orientation.

34. The method of claim 33, wherein the determined orientation is likely indicative of a pressure between the external charger and a patient's tissue.

* * * * *